United States Patent
Von Der Haar

(10) Patent No.: US 6,823,038 B2
(45) Date of Patent: Nov. 23, 2004

(54) X-RAY DETECTOR ARRAY AND METHOD FOR MANUFACTURING SAME

(75) Inventor: Thomas Von Der Haar, Nuremberg (DE)

(73) Assignee: Siemens Aktiengesellschaft, Münich (DE)

( * ) Notice: Subject to any disclaimer, the term of this patent is extended or adjusted under 35 U.S.C. 154(b) by 209 days.

(21) Appl. No.: 10/092,136

(22) Filed: Mar. 6, 2002

(65) Prior Publication Data

US 2002/0163992 A1 Nov. 7, 2002

(30) Foreign Application Priority Data

Mar. 6, 2001 (DE) .......................... 101 10 673

(51) Int. Cl.[7] .............................. G21K 1/12; G01T 1/20
(52) U.S. Cl. ........................ 378/19; 378/98.8; 250/367; 250/370.11
(58) Field of Search ................... 378/19, 98.8; 250/367, 250/370.11

(56) References Cited

U.S. PATENT DOCUMENTS

| | | | | |
|---|---|---|---|---|
| 4,897,788 A | * | 1/1990 | King ........................... 378/12 |
| 4,969,166 A | * | 11/1990 | Hahn ........................... 378/19 |
| 5,227,633 A | * | 7/1993 | Ryuo et al. .................. 250/367 |
| 5,296,163 A | | 3/1994 | Leppert et al. ........ 252/301.4 S |
| 5,418,377 A | * | 5/1995 | Tran et al. ................ 250/483.1 |
| 5,440,129 A | | 8/1995 | Schmidt ...................... 250/366 |
| 5,519,227 A | * | 5/1996 | Karellas .................. 250/483.1 |
| 5,831,269 A | * | 11/1998 | Nakamura ................... 250/367 |
| 5,867,554 A | | 2/1999 | Hupke ............................ 378/4 |
| 5,981,959 A | * | 11/1999 | Apte ........................ 250/483.1 |
| 6,005,908 A | * | 12/1999 | Oppelt et al. .................. 378/19 |

FOREIGN PATENT DOCUMENTS

WO  WO 00/43810  7/2000

\* cited by examiner

*Primary Examiner*—Allen C. Ho
(74) *Attorney, Agent, or Firm*—Schiff Hardin LLP

(57) ABSTRACT

A detector array for detecting X-rays has a number of sensor elements that each have a scintillator element, which is sensitive to X-rays, and a photo-electrical transducer optically coupled thereto. An intermediate areas separating adjacent scintillator elements from one another is present between each two adjacent scintillator elements. Scintillator material is present in the intermediate area. In a production method for such a detector array for detecting X-rays, separating channels are introduced into a layer that is composed of scintillator material, which is sensitive to X-rays, without completely separating the layer.

14 Claims, 2 Drawing Sheets

X-RAY DETECTOR ARRAY AND METHOD FOR MANUFACTURING SAME

BACKGROUND OF THE INVENTION

1. Field of the Invention

The present invention relates to a detector array for detecting X-rays of the type having a number of individual detector elements that are arranged in a two-dimensional matrix or a row, each detector element having a scintillator element, which is sensitive to X-rays, and a photo-electrical transducer having in optical coupling therewith, with an intermediate area separating the scintillator elements from one another between each two adjacent scintillator elements.

The invention also relates to a method for operating such a detector array and to a production method for a detector array for detecting X-rays.

2. Description of the Prior Art

Luminous or scintillator material is used for computed tomography apparatuses and in other devices in which X-rays or other high energy radiation is to be detected by detectors, the luminous or scintillator material converts X-rays or other high energy radiation into other electromagnetic radiation in a spectral range discernable to the human eye or to a photo-electrical receiver. The detected electromagnetic radiation can be visible light, ultraviolet light or infrared light, for example. For example, U.S. Pat. No. 5,296,163 describes a suitable scintillator material, referred to as UFC (Ultra Fast Ceramic).

Detectors that are structured in at least one direction are necessary for obtaining a local resolution of the X-ray signal. For example, detector arrays are used in which a number of sensor elements are arranged in the manner of a row (linear detector array or one-dimensional detector array).

For a faster image processing and for an improved utilization of the X-ray bundle radiated from an X-ray source, it is also known to fashion an X-ray detector such that it is structured along two axes perpendicular onto one another, so that a two-dimensional detector array is formed. For example, U.S. Pat. No. 5,440,129, European Patent No. 0 819 406 A1 and WO 00/43810 disclose such two-dimensional detector arrays having the individual sensor elements arranged in the manner of a matrix.

A sensor element is composed of a scintillator element, which is sensitive to X-rays, and of a photo-electrical transducer in optical coupling therewith, such as a photodiode or a CCD element.

In known detector arrays, the individual scintillator elements are formed with an intermediate area separating them from one another that is filled with a reflector material and/or absorber material, and/or the sides of the adjacent scintillator elements facing the intermediate area are provided with a reflective coating. Crosstalk between adjacent scintillator elements, which is the transfer of light from a scintillator element into an adjacent scintillator element, thus is prevented. In this way, the light quanta generated by an X-ray quantum in a scintillator element, with high efficiency, exclusively reach the photo-electrical transducer that is allocated to that scintillator element without generated light quanta reaching the photo-electrical transducer of an adjacent scintillator element to a significant extent. A best possible spatial resolution is thus achieved.

The presence of the intermediate areas necessary for the structuring, however, reduces the geometric efficiency of the detector array. The X-ray quanta striking the intermediate areas between scintillator elements do not generate light quanta and thus are not registered.

SUMMARY OF THE INVENTION

An object of the present invention is to provide a detector array that is of high efficiency and has a sufficient spatial resolution. A further object is to provide a method for operating such a detector array and a production method for such a detector array.

The first object is achieved in accordance with the invention in a detector array, wherein scintillator material is present in the intermediate area.

The adjacent scintillator elements are preferably connected to one another by a compound or connection that is composed of scintillator material and that penetrates through the intermediate area.

It has been previously assumed that a complete optical insulation between adjacent scintillator elements is necessary in order to be able to operate a detector array of the aforementioned type for detecting X-rays. The invention is based on the realization that although the spatial resolution is slightly negatively affected with respect to an incomplete optical insulation of adjacent scintillator elements, the efficiency of the detector array is improved to an extent that outweighs the decrease in resolution. An explanation is that the light quanta, which are generated in the intermediate area of arriving X-ray quanta in the scintillator material, partially proceed into one of the adjacent scintillator elements and partially reach into the other adjacent scintillator element, however, it is extremely unlikely that such light quanta reach into the following scintillator elements, i.e. into the scintillator elements after next. In other words, the X-ray quanta radiating into the intermediate area not only generate a constant offset or background, increasing the brightness of the image, but also contribute to the resolution. Therefore, the inventive detector array has an efficient spatial resolution and is highly efficient. These two variables are optimized with respect to each other, although each variable does not have the best possible value by itself. Therefore, new application possibilities result for the inventive detector array.

The photo-electrical receivers, which are respectively allocated to a scintillator element, can be photodiodes, CCD elements and/or CMOS detectors, for example.

In an embodiment, a portion of each intermediate area between two adjacent scintillator elements in the inventive detector array is fashioned as a separating area or insulating area for the optical insulation, namely for reducing crosstalk between the adjacent scintillator elements. In a different section of the intermediate area, the compound composed of scintillator material fills the intermediate area.

The compound is fashioned as a bridge or web. The other sections in the intermediate area, namely the insulating or separating area, can be fashioned as a separation layer filled with a reflector material or absorber material, for example. The intermediate area alternatively can be composed of only a thin reflecting layer deposited onto one side or both sides of the scintillator elements facing the intermediate area. The separating or insulating area alternatively can be fashioned as an air-filled separating space, particularly with adjacent reflective coatings.

In a preferred embodiment, the adjacent scintillator elements and the compound between the scintillator elements are formed from a common piece of scintillator material. Such a detector array can be advantageously produced in an extremely simple way, since the individual scintillator elements, during the production, do not have to be individualized into pixels that are insulated from one another. A coherent array of scintillator elements can be maintained which can be operated in a more simple way.

Preferably, the insulating area only partially extends across the sides of the adjacent scintillator elements facing one another.

In another preferred embodiment, the height of the compound composed of scintillator material has a value from the range between 20% to 50% of the height of the scintillator elements.

Preferably, the height of the compound is fashioned such that the mathematical product from this height, with the X-ray absorption coefficient of the scintillator material, has a value from the range between 0.15 and 0.50.

Given a height in the indicated ranges, the resolution that is required for use for medical X-ray image acquisition still can be obtained, since the occurring crosstalk is still tolerable. On the other hand, a large portion of the X-ray quanta radiating into the intermediate area is already absorbed in the compound or in the web composed of scintillator material and contributes to the useful signal. As a result, an improvement of the quanta efficiency or of the efficiency of the detector is also obtained in addition to the sufficient spatial resolution.

The scintillator material in the intermediate are is preferably arranged on the side of the detector array facing away from the X-ray reception side. Such an arrangement is more advantageous for the spatial resolution than if the scintillator material were arranged at the reception side in the intermediate area.

In the aforementioned two-dimensional detector array, the object of the invention is inventively achieved by the scintillator material being present in the intermediate area between rows.

Preferably, the intermediate area between columns is free of scintillator material.

Such a two-dimensional detector array is particularly suitable for a computed tomography apparatus. In a computed tomography apparatus, the rows are preferably oriented in the circumferential direction, referred to as the (p-direction (detector channel direction) of the computed tomography apparatus, and the columns are oriented in the direction of a patient to be examined, referred to as the z-direction of the computed tomography apparatus.

The object relating to an operating method is inventively achieved in that crosstalk caused by the scintillator material in the intermediate area is taken into consideration during the image calculation or image evaluation following the detection of the X-rays.

Given the use of the detector array in a computed tomography apparatus, the crosstalk level is calculated during the image reconstruction. A mathematical convolution method having a corresponding convolution kernel (convolution function) can be used for this purpose.

The consideration of crosstalk during the image calculation or image evaluation has the advantage that the loss in the spatial resolution as a result of the scintillator material in the intermediate area can be kept extremely low.

The object relating to a production method for a detector array for detecting X-rays is inventively achieved in a method wherein separating channels are introduced into a layer that is composed of scintillator material, which is sensitive to X-rays, without completely separating the layer, with scintillator elements separated from one another by the separating channels being coupled with a photo-electrical transducer.

The separating channels are introduced by sawing or milling, for example.

A separate carrier for the individual pixels or scintillator elements is not necessary, since a coherent array of individual pixel elements or detector elements is maintained as a result of the only incomplete separation of the layer, so that the array can be further processed in a simple way.

A reflector material and/or absorber material for light is preferably introduced into the separating channels.

DESCRIPTION OF THE PREFERRED EMBODIMENTS

Figure 1:
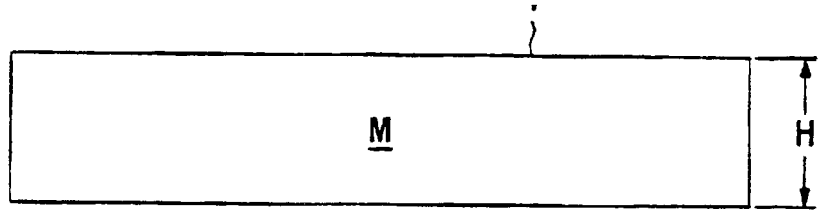
FIG. 1 shows a first step of the inventive production method.

The production of an inventive detector array—as shown in FIG. 1—is based on a rectilinear layer 1 composed of scintillator material M. For example, the scintillator material M is of the type referred to as UFC, as described in U.S. Pat. No. 5,296,163. The height H of the layer 1 is approximately 0.1 cm.

Figure 2:
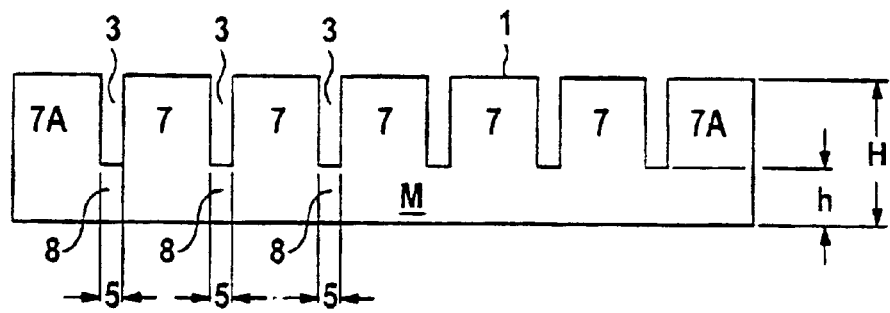
FIG. 2 shows a second step of the inventive production method.

As shown in the result of FIG. 2, separating channels 3, which are parallel to one another and perpendicular to the plane of the drawing, in a second step, are sawed or milled into the layer 1 from above. Each separating channel 3 is a part of an intermediate area 5 by which individual scintillator elements 7 are separated from one another.

The separating channels 3 have a depth that is smaller than the height H of the scintillator elements 7. The height h of remaining compounds 8 from scintillator material M between adjacent scintillator elements 7 is approximately 0.03 cm.

Therefore, the connections 8 fashioned as bridges or webs are a part of the intermediate areas 5, so that scintillator material M is present in these intermediate areas 5.

Figure 3:
FIG. 3 shows a third step of the inventive production method.
Figure 3:
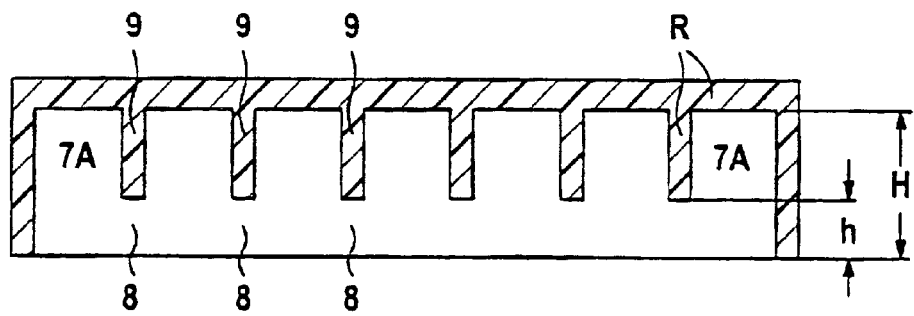

FIG. 3 shows the result of a third step of the production method. In this step, the separating channels 3, the side faces of the scintillator elements 7A situated most remote and the side faces that can be faced toward the X-rays 10 to be detected are filled or covered with a reflector material and/or absorber material R. The separating channels 3 thus become insulating areas 9 which reduce crosstalk between adjacent scintillator elements 7, 7A.

Figure 4:
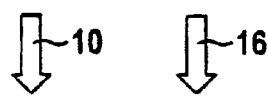
FIG. 4 shows a fourth step of the inventive production method with the detector array as the end product.
Figure 4:
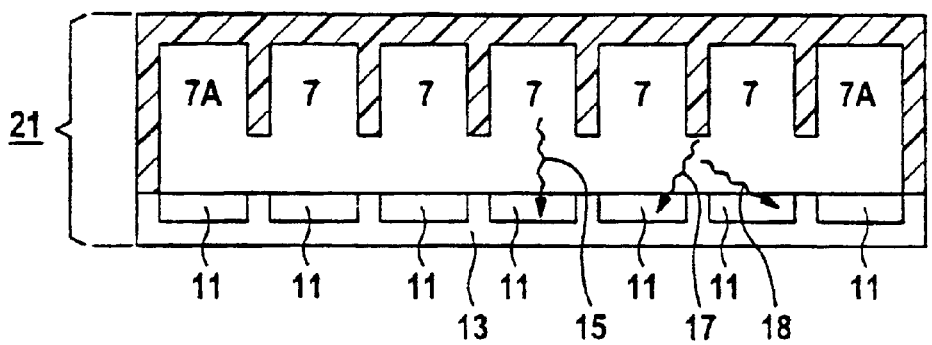

FIG. 4 shows the end product resulting from a fourth step of the production method. In the fourth step, a substrate 13 having individual photo-electrical receivers 11 is optically coupled to the side of the scintillator elements 7 facing away from the X-rays 10. An optically transparent adhesive, for example, is used for this purpose. Respectively one photo-electrical transducer 11 is allocated to one of the scintillator elements 7 in position and size. The light quanta 15 generated by the arriving X-rays 10 in the scintillator elements produce an electrical signal in the respective photo-electrical transducers 11. Those electrical signal are supplied via contacts (not shown) of an evaluation electronic unit.

X-ray quanta 16 radiating into the insulating area 9 also generate light quanta 17, 18, namely in the compound 8. These light quanta 17, 18 arrive at adjacent transducers 11.

The end product of the production method shown in FIG. 4 shows an inventive one-dimensional detector array.

Figure 5:
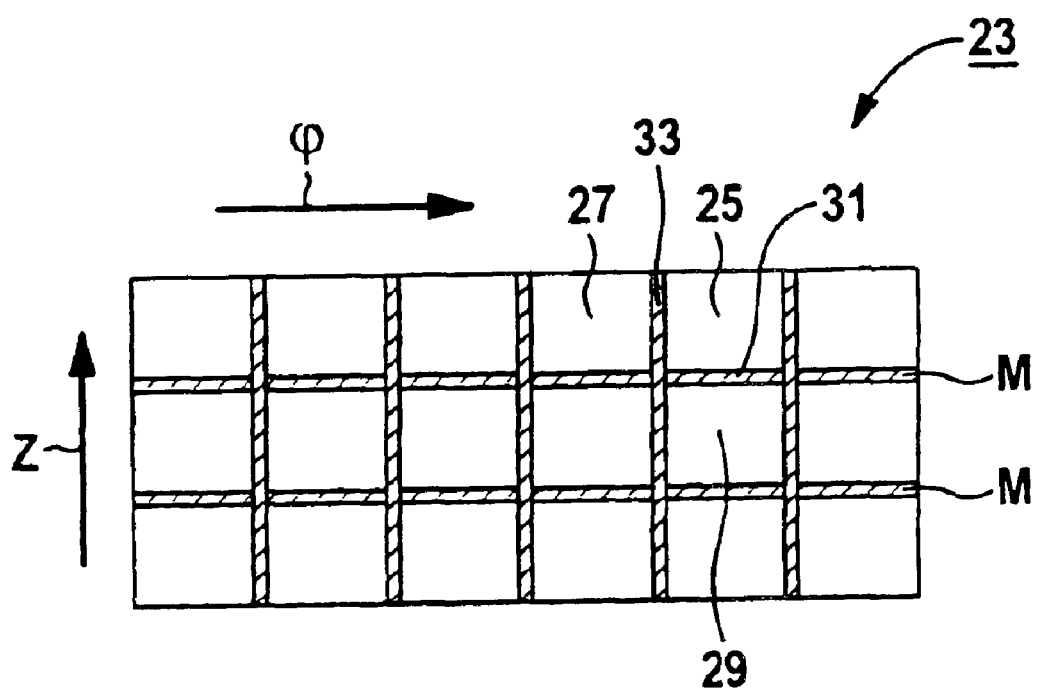
FIG. 5 shows an inventive two-dimensional detector array in a plan view.

Analogous to the FIGS. 2 and 3, separating channels and insulating areas are introduced perpendicular to the separating channels 3 or insulating areas 9 shown therein such that they intersect in order to generate a two-dimensional, matrix-like detector array 23 (see explanations of FIG. 5).

In the inventive detector array 21, the scintillator layer 1 is not structured in full depth. A compound 8 or a web composed of scintillator material M remains between the individual pixels or scintillator elements 7. An optical separation of the pixels is still assured, although not in a complete manner. A large portion of the X-ray quanta striking the intermediate area 5 between two pixels is absorbed in the scintillator web, so that the efficiency of the detector array 21 is improved. The depth of the structuring depends on the level of the tolerable crosstalk and on the absorption properties of the scintillator material M. Some crosstalk is tolerable when—given a constant and known crosstalk—the crosstalk effect, in the image reconstruction, is "calculated out" of the computed tomography image by convolution with a suitable convolution kernel, for example. The absorption properties of the scintillator material M determine how many quanta are absorbed in the connection 8 or in the web. Approximately 50% of the arriving X-ray quanta are absorbed by a web having a thickness of only h=0.03 cm, for example, given an absorption coefficient of 10 cm$^{-1}$. These X-ray quanta contribute to the useful signal. Therefore, the quanta efficiency of the detector array 21 is increased in comparison to a detector array having pixels that are completely separated from one another. The spatial resolution of the detector array 21 is maintained at the same time. Such a detector array 21 is particularly advantageous in modern multi-slice computer tomography apparatuses having a number of separating channels.

FIG. 5 shows a schematic plan view of an inventive two-dimensional detector array 23. It is composed, for example, of 6×3 individual sensor elements arranged in three rows and six columns. The individual sensor elements each have—see the one-dimensional detector array 21 of FIG. 4—a scintillator element and an allocated photo-electrical receiver. As an example, three scintillator elements are referred to as 25, 27, 29.

The detector array 23 is installed into a computed tomography apparatus (not shown) such that the rows are oriented in the (φ-direction (detector channel direction) of the computed tomography apparatus, i.e., in the circumferential direction of an X-ray emitter rotating on a gantry. The columns extend in the z-direction, i.e., in the direction of the patient.

In the two-dimensional detector array 23 of FIG. 5, scintillator material M is present in the intermediate areas 31 generating the insulation between the scintillator elements 25, 29 in one of the two array dimensions. In the second dimension, scintillator material M is not present in the intermediate area 33 between the scintillator elements 25, 27.

The preferred and exemplary embodiments described in connection with the one-dimensional detector array 21 are also valid for the two-dimensional detector array 23.

Although modifications and changes may be suggested by those skilled in the art, it is in the intention of the inventor to embody within the patent warranted hereon all changes and modifications as reasonably and properly come within the scope of his contribution to the art.

I claim as my invention:

1. An X-ray detector comprising:

a plurality of individual sensor elements, each sensor element including an X-ray sensitive scintillator element which emits light dependent on X-rays incident thereon and a photo-electrical transducer optically coupled to said scintillator element for generating an electrical signal corresponding to said light;

said sensor elements being disposed in an arrangement wherein each scintillator element is adjacent to another scintillator element, said arrangement having intermediate areas separating adjacent scintillator elements; and scintillator material disposed in said intermediate areas said scintillator material having a height in said intermediate areas and an X-ray absorption coefficient, and a mathematical product of said height of said scintillation material in said intermediate areas and said X-ray absorption coefficient having a value in a range between 0.15 and 0.50.

2. A detector as claimed in claim 1 wherein said arrangement is a linear array.

3. A detector as claimed in claim 1 wherein said arrangement is a matrix array.

4. A detector as claimed in claim 1 wherein said adjacent scintillator elements are connected to each other by a compound which includes said scintillator material and which extends through said intermediate areas.

5. A detector as claimed in claim 4 wherein said adjacent scintillator elements and said compound are formed by a common piece of scintillator material.

6. A detector as claimed in claim 1 wherein said intermediate areas include an insulating area for reducing crosstalk between said adjacent scintillator elements, and wherein said insulation area extends only partially between respective sides of said adjacent scintillator elements facing each other.

7. A detector as claimed in claim 1 wherein said material is a scintillator material compound areas, said compound having a height in said intermediate area in a range between 20% through 50% of a height of said adjacent scintillator elements.

8. A detector as claimed in claim 1 wherein said sensor elements each have a side adapted to receive X-rays, and wherein said scintillator material is disposed in said intermediate areas at a side of said arrangement facing away from the respective sides of said sensor elements adapted to receive X-rays.

9. A two-dimensional X-ray detector comprising:

a plurality of individual sensor elements disposed in an arrangement of a plurality of intersecting rows and columns, each sensor element including an X-ray sensitive scintillator element which emits light dependent on X-rays incident thereon and a photo-electrical transducer optically coupled to said scintillator element for generating an electrical signal corresponding to said light;

each scintillator element in said arrangement being adjacent to another scintillator element, said arrangement having intermediate areas separating adjacent scintillator elements; and scintillator material disposed in at least some of said intermediate areas between adjacent scintillator elements in said rows, with respective intermediate areas between adjacent columns of said sensor elements being free of said scintillator material.

10. A computed tomography apparatus comprising:

a radiation source which emits X-rays from a focus, at least said focus being rotatable around a system axis in a circumferential direction;

a two dimensional detector for detecting said X-rays, comprising a plurality of individual sensor elements disposed in an arrangement of a plurality of intersecting rows, disposed parallel to said system axis, and columns, disposed in said circumferential direction, each sensor element including an X-ray sensitive scintillator element which emits light dependent on X-rays incident thereon and a photo-electrical transducer optically coupled to said scintillator element for generating an electrical signal corresponding to said light, each scintillator element in said arrangement being adjacent to another scintillator element, said arrangement having intermediate areas separating adjacent scintillator elements, and scintillator material disposed in said intermediate areas between adjacent scintillator elements in said rows, with respective intermediate areas between adjacent columns of said sensor elements being free of said scintillator material; and an image reconstruction system for reconstructing an image from said electrical signals.

11. A method for manufacturing a detector for detecting X-rays comprising the steps of:

providing a layer of scintillator material;

selectively removing scintillator material from said layer to produce a plurality of separating channels with individual sensor elements respectively between said separating channels, said separating channels extending only partly through said layer to form a portion of respective intermediate areas between adjacent sensor elements, with a remainder of the intermediate areas formed by said scintillator material, each of said sensor elements having a sensor element face adapted to receive incoming X-rays, said layer having a layer side opposite to the respective faces;

disposing a plurality of optoelectric transducers at said layer side, with the optoelectric transducers being respectively optically coupled to the individual sensor elements; and filling at least some of said intermediate areas with scintillator material, having an X-ray absorption coefficient, to a height so that a product of said height and said absorption coefficient is in a range between 0.15 and 0.50.

12. A method as claimed in claim 11 comprising additionally introducing a light reflective material into each of said separating channels.

13. A method as claimed in claim 11 comprising additionally introducing a light absorption material into each of said separating channels.

14. A method as claimed in claim 11 wherein the step of filling at least some of said intermediate areas with scintillator material comprises filling at least some of said intermediate areas with scintillator material compound, and filling at least some of said intermediate areas with said scintillator material compound to a height in said at least some of said intermediate areas in a range between 20% through 50% of a height of said adjacent scintillator elements.

* * * * *